(12) United States Patent
Schwartz et al.

(10) Patent No.: US 7,682,079 B2
(45) Date of Patent: Mar. 23, 2010

(54) MEDICAL IMAGING SYSTEM AND METHOD WITH INTEGRATED WEIGHT SENSING

(75) Inventors: Matthew Richard Schwartz, Oconomowoc, WI (US); Richard Coe, Sussex, WI (US); Roy Frisque, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/061,464

(22) Filed: Apr. 2, 2008

(65) Prior Publication Data

US 2009/0252300 A1 Oct. 8, 2009

(51) Int. Cl.
*A61B 6/04* (2006.01)
*H05G 1/54* (2006.01)

(52) U.S. Cl. .................................. 378/209; 378/117
(58) Field of Classification Search ......... 378/208–209; 5/600, 601; 600/415, 427
See application file for complete search history.

(56) References Cited

U.S. PATENT DOCUMENTS 6,026,318 A * 2/2000 Bernstein et al. ............ 600/427
7,293,308 B2 * 11/2007 Everett et al. ................... 5/601
7,458,118 B2 * 12/2008 Bak ................................ 5/601
2007/0076842 A1 * 4/2007 Tkaczyk et al. ................ 378/5

* cited by examiner

*Primary Examiner*—Hoon Song
(74) *Attorney, Agent, or Firm*—Fletcher Yoder PC (57) ABSTRACT

An integrated weight sensing system and method is disclosed for a medical imaging system. In one embodiment, the integrated weight sensing system may include a table assembly, a load cell, and a processor that are implemented in a medical imaging system. The table assembly includes a lifting mechanism used to position a patient within the medical imaging system. The load cell is mechanically coupled to the table assembly and in communication with the processor. The load cell is configured to measure and indicate the weight of the patient and the processor may be configured to adjust imaging parameters based on the weight of the patient. The table assembly may include a device in communication with the load cell and/or processor to display the weight of the patient. Additionally, the table assembly and/or the processor may include an interface for zeroing or recalibrating the load cell.

27 Claims, 5 Drawing Sheets

MEDICAL IMAGING SYSTEM AND METHOD WITH INTEGRATED WEIGHT SENSING

BACKGROUND

The invention generally relates to medical imaging system and methods. More specifically, embodiments of the invention relate to an integrated weight sensing system for automatically measuring the weight of a patient and communicating the weight of the patient to a medical imaging system.

Medical imaging modalities make use of different physical phenomena to acquire medical images. For example, magnetic resonance imaging (MRI) systems use non-ionizing radio frequency (RF) signals to generate emissions from gyromagnetic material to acquire image data. In contrast, X-ray systems, and other modalities employing X-rays such as computed tomography (CT) systems use ionizing X-rays to acquire image data. Other modalities, such as positron emission tomography (PET) systems, ultrasound imaging systems, and so forth, are based upon still other physical phenomena. Regardless of the imaging modality, the quality of the image data, or the particular settings of the system are a function of the weight or mass of the patient. A heavier patient (i.e., one with more mass) requires system settings different from those of a smaller patient to obtain the same quality image. Thus, medical imaging systems may be configured to increase the power or dose of the radiation, or to adjust other image acquisition factors depending on the weight or mass of the patient that is undergoing the scanning procedure.

Medical imaging systems often require the medical technician to manually enter the weight of the patient to determine the radiation dose rate. This increases the potential for error and may result in the technician improperly configuring the imaging system based on an errant weight entry, incorrect weight measurement, and so forth. When this occurs, image quality suffers, or the patient has to undergo additional scans to obtain the desired image quality, thereby exposing the patient to additional inconvenience and, in certain modalities, greater doses of radiation. Furthermore, additional scans are costly, and inefficient. There is a need in the art for an integrated weight sensing system that automatically measures the weight of a patient and communicates the measurement to the medical imaging system to allow for proper setting of the system during image acquisition.

BRIEF DESCRIPTION

Embodiments of the present invention provide an integrated weight sensing system and method for medical imaging systems. The integrated weight sensing system may include a table assembly, a load cell, and a processor implemented in a medical imaging system. The medical imaging system may be of any modality, including CT systems, PET systems, MRI systems, and so forth. The table assembly may include a lifting mechanism used to position a patient within the medical imaging system. The table assembly may also include a base, an upper table, and a scanning table. The base may be coupled to the upper table via linkages and the lifting mechanism. The scanning table may be supported by the upper table and configured to move parallel to the upper table and may cantilever therefrom. The base of the table may include a fixed clevis that is coupled to a rotating clevis of the lifting mechanism. The load cell may be mechanically coupled to the fixed clevis or any portion of the base. Alternatively, the load cell may be coupled to the rotating clevis of the lifting mechanism or any portion of the lifting mechanism. The lifting mechanism may include various mechanical systems, such as a screw drive or hydraulic cylinder.

The load cell may be in communication with the processor and may be mechanically coupled to the table assembly. The load cell may be configured to measure and indicate the weight of the patient and the processor may be configured to adjust imaging parameters based on the weight of the patient. The load cell may include strain gages with the gages electrically coupled in a Wheatstone bridge configuration. Additionally, the Wheatstone bridge may be oriented to detect multi-component loading. The table assembly may include a device in communication with the load cell and/or processor to display the weight of the patient. Additionally, the table assembly and/or the processor may include an interface for zeroing or recalibrating the load cell.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
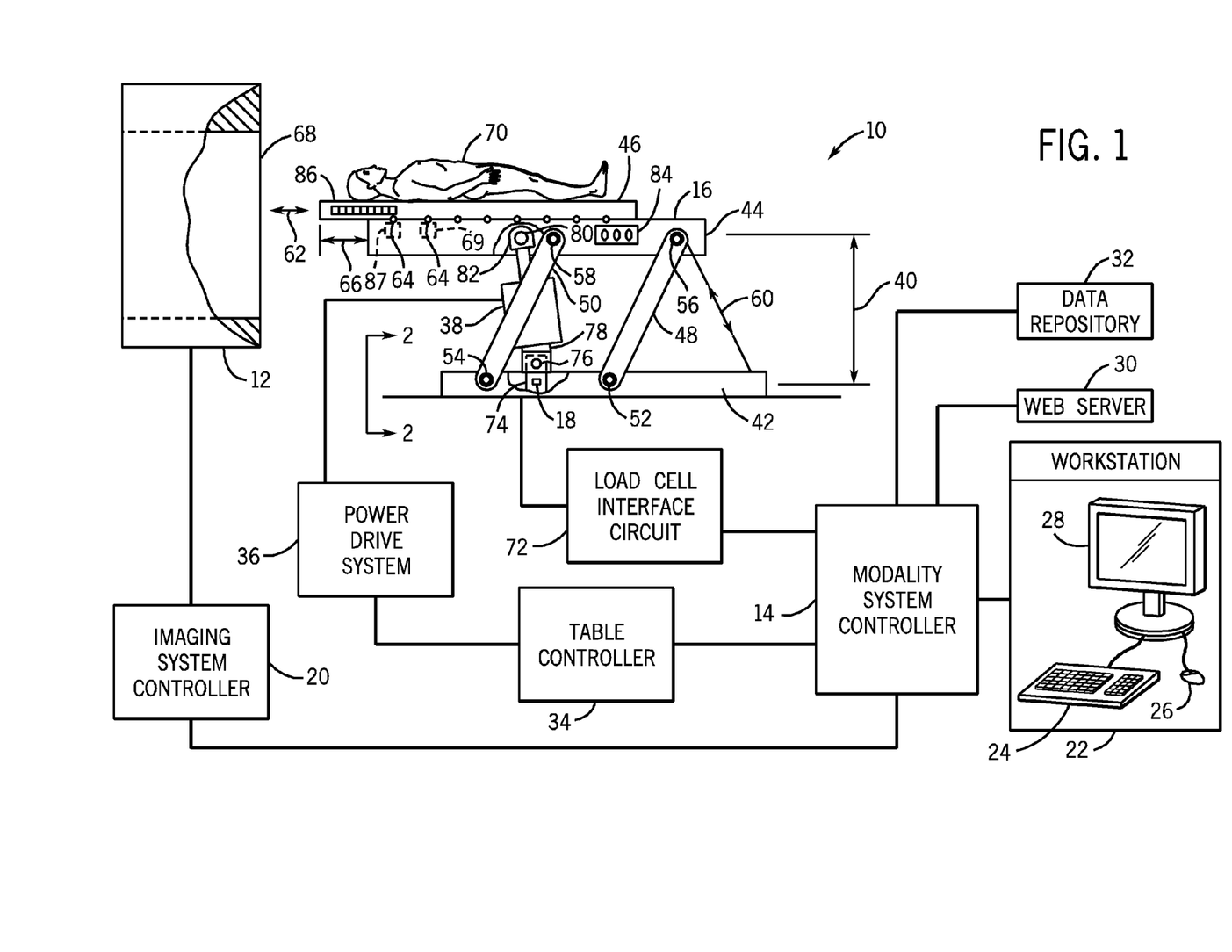
FIG. 1 is a general overview of an integrated weight sensing system for a medical imaging system in accordance with certain aspects of the present techniques.

Turning now to the drawings and referring first to FIG. 1, an exemplary embodiment of a medical imaging system with an integrated weight sensing system is illustrated and designated generally by reference numeral 10. System 10 generally includes an imaging system 12, a system controller 14, and a table assembly 16 with an integrated weight sensing element, such as a load cell 18. Imaging system 12 may be a CT system, a PET system, an MRI system, or any other suitable imaging modality. Imaging system 12 may be controlled by an imaging system controller 20 that may be further coupled to modality system controller 14. Modality system controller 14 and imaging system controller 20 may be included in a single unit and directly integrated into the imaging modality system 12 or may be separate from the system 12 and positioned remotely, such as via network cables.

A workstation 22 may be coupled to modality system controller 14 to enable an operator to interface with modality system controller 14. Workstation 22 may include user interface devices, such as a keyboard 24, a mouse 26, and/or a monitor or display 28. Workstation 22 can be used for a variety of purposes such as enabling an operator to control medical imaging system 12, receive image data from imaging system 12, and/or process the image data. Additionally, interface devices 24, 26, 28 may also be integrated into the imaging system 12 or connected to imaging system 12 via network cables. Likewise, both imaging system 12 and workstation 22 may be connected to a network. The network may include a web server 30 that enables remote access to imaging system 12. The network may also include a data repository 32 that enables imaging system 12 or workstation 22 to retrieve or store images.

System controller 14 may be coupled to table 16 via table controller 34. Table controller 34 may be used to position table 16 via power drive system 36 that is coupled to a lifting mechanism 38 to position the table at a desired height 40. Lifting mechanism 38 may include a hydraulic cylinder, a screw drive cylinder or any suitable lifting device. In other words, power drive system 36 may include different components depending on the configuration of lifting mechanism 38. For example, if lifting mechanism 38 is a screw drive cylinder then power drive system 36 will include an electrical drive component or motor. Similarly, if lifting mechanism 38 is a hydraulic cylinder then power drive system 36 will include a hydraulic system for providing a flow of pressurized fluid to the lifting cylinder. In sum, lifting mechanism 38 is used to adjust the height of table assembly 16, generally represented by reference numeral 40, via power drive system 36. Embodiments of the present invention are not limited to a specific type of lifting mechanism implemented in imaging system 12. In other words, embodiments of the present invention may be used with a variety of different lifting mechanisms 38 and are not limited to either a screw drive or hydraulic system.

Table assembly 16 may include a base 42, an upper table or support 44, and a scanning table 46. Base 42 is generally fixed in position where upper table 44 and scan table 46 may be moved to various positions with respect to base 42. Specifically, linkages 48, 50 constrain the upper table 44 and scanning table 46 to base 42. Linkages 48, 50 may include a clevis and pin connection 52, 54 at the base and a clevis and pin connection 56, 58 at the upper table. Linkages 48, 50 ensure the motion of the upper table with respect to the base follows a fixed path, generally represented by reference numeral 60.

In certain systems, scanning table 46 may be made from a lower density material than that of upper table 44. The lower density material reduces the radiation absorption and power requirements of the imaging system. Scanning table 46 is generally configured to move relative to upper table 44, generally represented by reference numeral 62, via rollers 64 or other suitable devices. In other words, scanning table 46 may cantilever from upper table 44, as indicated by reference numeral 66. This enables scanning table 46 to extend into bore 68 of imaging system 12. Again, this is advantageous because scanning table 46 may be made from a composite material or similar material that does not affect the image quality. Further, in various embodiments, scanning table 46 may be manually extended and retracted by a user with respect to upper table 44, or an actuator 69 may control such movement in response to an input signal, such as a signal generated by a user via workstation 22, automatically generated by the modality system controller 14 or table controller 34, or the like.

FIG. 1 further illustrates a patient 70 positioned on scanning table 46. Both upper table 44 and scanning table 46 are shown at the proper height position 40 to position patient 70 into bore 68 of imaging system 12. The distance 66 that scanning table 46 may be extended beyond the edge of upper table 44 is a function of the weight of the patient 70. A patient who weighs more requires that table 46 be extended a shorter distance 66 than a patient who weighs less. One of the problems with current systems is that they do not provide an accurate way to determine the weight of the patient. Moreover, the distance that scanning table 46 may be extended may not be readily known to the operating technician. In other words, current systems do not provide a reliable means of preventing scanning table 46 from being damaged due to overextension. Therefore, not only is the weight of the patient important for dose calculations, but the weight of the patient may be important for physically positioning the patient in the bore of the imaging system.

Embodiments of the present invention may use the weight measurement determined by load cell 18 for a number of purposes. Specifically, the weight of patient 70 may be used to automatically configure the radiation dose or other settings of imaging system 12, depending upon the particular modality and the settings that are affected by patient weight, size or mass. This is accomplished by coupling load cell 18 to a load cell interface circuit 72. Load cell interface circuit 72 is further coupled to modality system controller 14 and provides a signal indicative of the weight of patient 70 so that the controller or operator may determine the proper radiation dose. For example, when patient 70 is placed on scanning table 46, load cell 18 will detect the weight of the patient and communicate that weight to modality system controller 14 via load cell interface circuit 72. The operator may then optimize operating parameters (e.g., radiation dose value) of imaging system 12 or the modality system controller 14 may do this automatically. This may improve overall image quality and reduce the additional scans required because of an incorrectly configured imaging system.

FIG. 1 illustrates load cell 18 positioned on, and mechanically coupled to, fixed clevis 74 of base 42. Further, lifting mechanism 38 may be coupled to fixed clevis 74 via pin 76 and rotating clevis 78. Similarly, lifting mechanism 38 may be coupled to upper table 44 via pin 80 and clevis 82. In this configuration, lifting mechanism 38 may rotate about either pin 76 or 80 as table height 40 is adjusted. As discussed below, load cell 18 is not limited to the position shown in FIG. 1. For example, load cell 18 may be positioned on either rotating clevis 82 or rotating clevis 78 and is not limited to being located on fixed clevis 74. Further, load cell 18 may include foil strain gages configured in a Wheatstone bridge. The foil strain gages may be either directly bonded to a clevis 76, 78, 82 or may be contained in a separate housing that is mechanically coupled to table assembly 16.

System 10 may include a display 84 that provides an operator with an indication of the weight (or size or mass) of the patient 70. Display 84 could serve as an alternative feedback loop and interface to an operator. For example, display 84 may include functions for zeroing load cell 18, recalibrating load cell 18, or communicating with load cell interface circuit 72. Additionally, display 84 enables an operator to quickly determine the allowable distance 66 that scanning table 46 may be extended beyond the edge of upper table 44. Specifically, a scale 86 may be located on the side of scanning table 46 or upper table 44 that indicates maximum safe distance 66 given the weight of patient. For example, scale 86 may include a gradual scale of weight in pounds or kilograms (e.g., 155, 160, 175, 185, etc. pounds). The operator could then read display 84 and position scanning table 46 at the corresponding weight on scale 86. Such a scenario might include scanning table 46 that can be rated to support a given weight, such as 300 pounds, when it is fully extended, but can support a greater weight, such as 600 pounds when it is partially extended. An operator could position the patient on the table and determine the weight of the patient via load cell 18 and display 84. The operator could extend the table until the edge of the upper table 44 aligned with the corresponding weight on scale 86.

Additionally, in some embodiments, system 10 may be configured to automatically limit, based on the weight of the patient, the amount by which scanning table 46 is permitted to extend from upper table 44. For instance, system 10 may calculate a maximum extension distance for movement of scanning table 46 with respect to upper table 44 that is customized based on the weight of the patient, which may be automatically received from the load cell 18 or manually input by a user. In one embodiment, table assembly 16 may include an electromechanical interlock 87 that receives an input signal based on the maximum extension distance and physically prevents extension of scanning table 46 from upper table 44 beyond this threshold distance. In another embodiment, one or more controllers of system 10 that control extension and retraction of scanning table 46 via actuator 69 may be programmed or otherwise configured to automatically limit extension of scanning table 46 beyond the calculated maximum extension distance. It should be appreciated that such arrangements would allow for improved operation of the imaging system 12 for bariatric specific customers.

Figure 2:
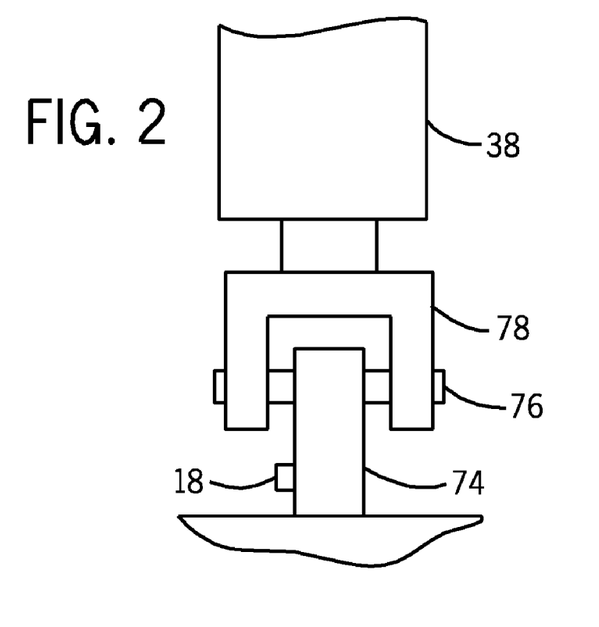
FIG. 2 is an elevational view of a fixed clevis and a rotating clevis of the table assembly of FIG. 1, viewed from line 2-2, illustrating a load cell mechanically coupled to the fixed clevis of the base of the table assembly.
Figure 3:
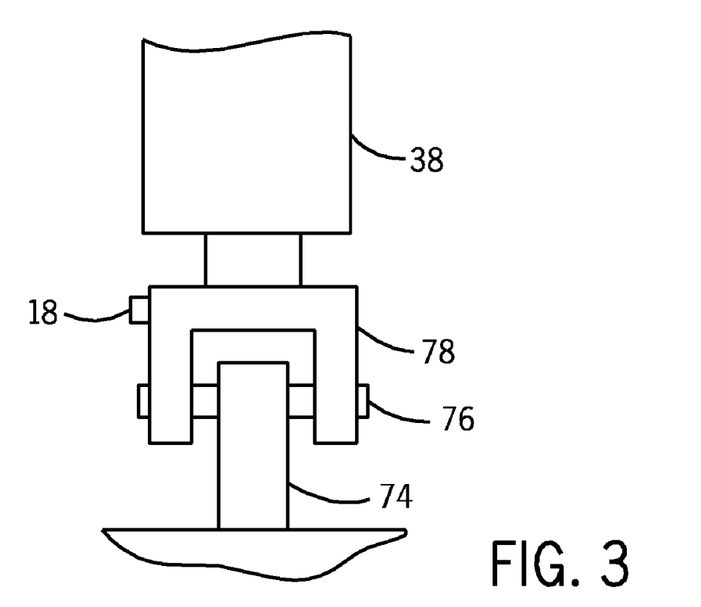
FIG. 3 is an elevational view of the fixed clevis and the rotating clevis of FIG. 2, illustrating a load cell mechanically coupled to the rotating clevis of the lifting mechanism.

FIGS. 2 and 3 illustrate possible locations where load cell 18 may be positioned to detect the weight of patient 70. Specifically, FIG. 2 illustrates load cell 18 positioned on fixed clevis 74 of base 42. In this embodiment, the weight of patient 70 is transferred from lifting cylinder 38 through rotating clevis 78 to pin 76 and further to fixed clevis 74. An advantage of this particular embodiment is that weight sensing element 18 is stationary and may not require angular corrections for weight as discussed below. Additionally, as illustrated in FIG. 3, load cell 18 may be positioned on rotating clevis 78. In this embodiment, the weight of patient 70 is transferred through lifting cylinder 38 to rotating clevis 78. This embodiment provides that the weight of patient 70 is directly measured via attachment to rotating clevis 78. In other words, there are fewer mechanical couplings and the weight is not distributed through pin 76 to fixed clevis 74.

FIGS. 2 and 3 illustrate two possible locations for load cell 18. However, embodiments of the present invention are not limited to these two locations. For example, referring to FIG. 1, load cell 18 may be positioned on upper rotating clevis 82, on upper table 44, or scanning table 46. In other words, embodiments of the present invention provide the advantage of enabling an operator to detect the weight of the patient but are not limited to specific locations of load cell 18. Likewise, embodiments of the present invention provide a load cell 18 that is specifically designed to operating with a screw drive or hydraulic cylinder for lifting mechanism 38.

Figure 4:
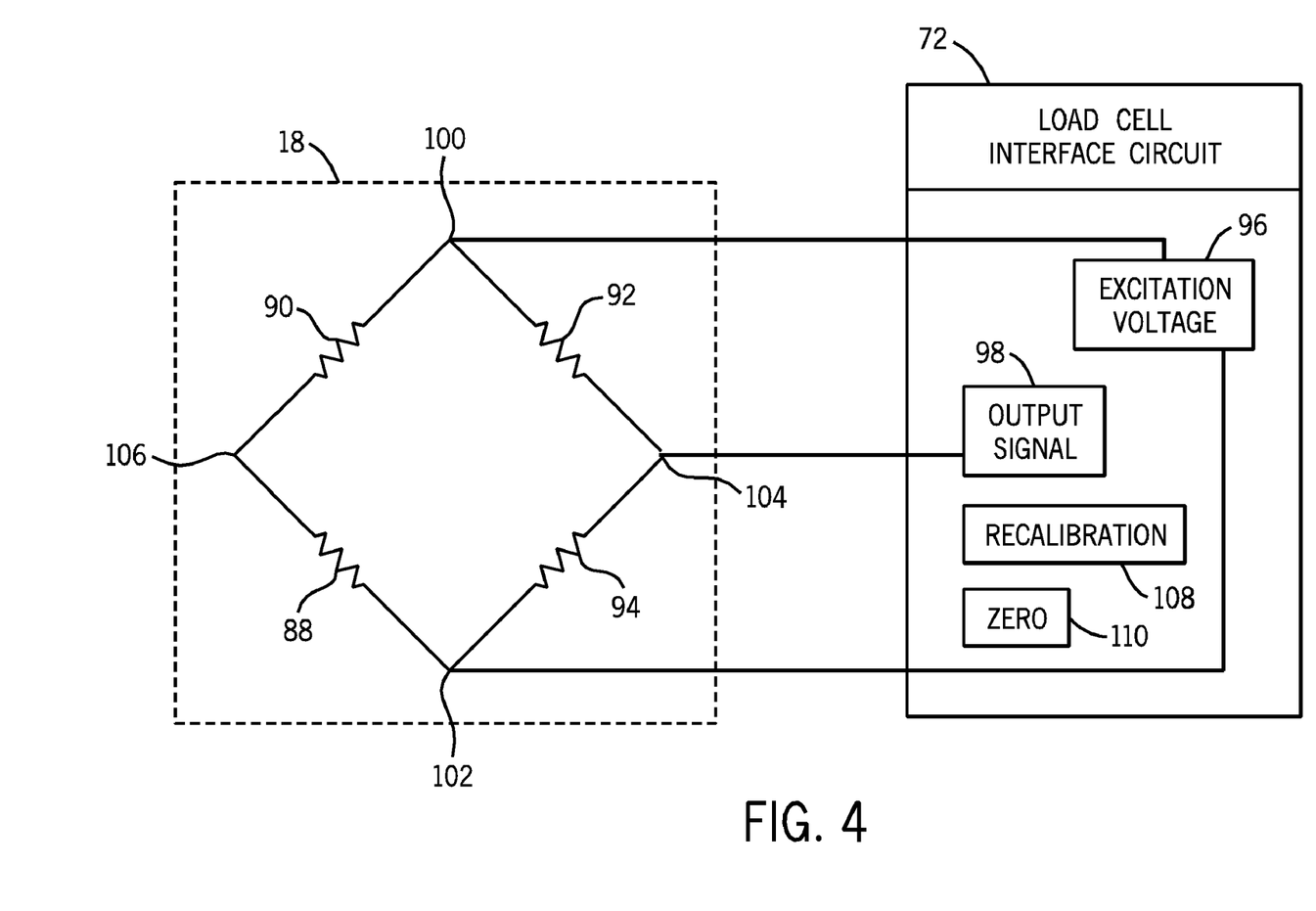
FIG. 4 is a schematic diagram of the load cell and load cell interface circuit system, illustrating a Wheatstone bridge configuration for the load cell and the electrical coupling of the bridge to the interface circuit.

FIG. 4 illustrates one embodiment of load cell 18 that is coupled to load cell interface circuit 72. Specifically, FIG. 4 illustrates four resistive elements 88, 90, 92, 94 configured in a Wheatstone bridge configuration. Each resistive element 88, 90, 92, 94 may be a foil strain gage, fixed resistor, or variable resistor. However, the resistance of at least one resistive element will be a function of the weight on the patient. Resistive elements 88, 90, 92, 94 may be directly bonded to clevis 74, 78, 82 or may be part of a pre-manufactured load cell. Additionally, resistive elements 88, 90, 92, 94 may be positioned to measure mechanical strain in different respective directions. In other words, resistive elements 88, 90, 92, 94 may be configured to correct for multi-component loading via the Wheatstone bridge.

Load cell interface circuit 72 may provide an excitation voltage 96 to load cell 18. In one embodiment, load cell interface circuit measures an output signal 98 of the Wheatstone bridge based upon the excitation voltage 96 and measured strain of resistive elements 88, 90, 92, 94. Specifically, load cell interface circuit 72 provides excitation voltage 96 across nodes 100 and 102. The output signal is then measured by coupling load cell interface circuit 72 to weight sensing element 18 via nodes 104 and 106. The output signal is a function of excitation voltage 96 and change in the resistance of resistive elements 88, 90, 92, 94 due to mechanical strain that is indicative of the weight of patient 70.

Further, load cell interface circuit 72 may include additional functions such as a recalibration function 108 or a zero function 110. The calibration function 108 may enable an operator to recalibrate weight sensing element 18 to correct for drift that may occur overtime. The drift can be either due to mechanical drift in load cell 18 or electrical drift in load cell interface circuit 72 or any of the other components of the system. Zero function 110 enables the user to eliminate or zero out the weight of the table and or other components to isolate the weight of the patient 70 (e.g., by applying an offset signal or value). In other words, display 84 may simply display weight of patient 70 without the weight of the upper table 44 or scanning table 46. This simplifies the measurement displayed on display 84 and does not require the operator to calculate or determine the weight of these or other components. This also may simplify the system by ensuring that modality system controller 14 receives the weight of patient 70 without having to correct for the weight of the table or other components.

Figure 5:
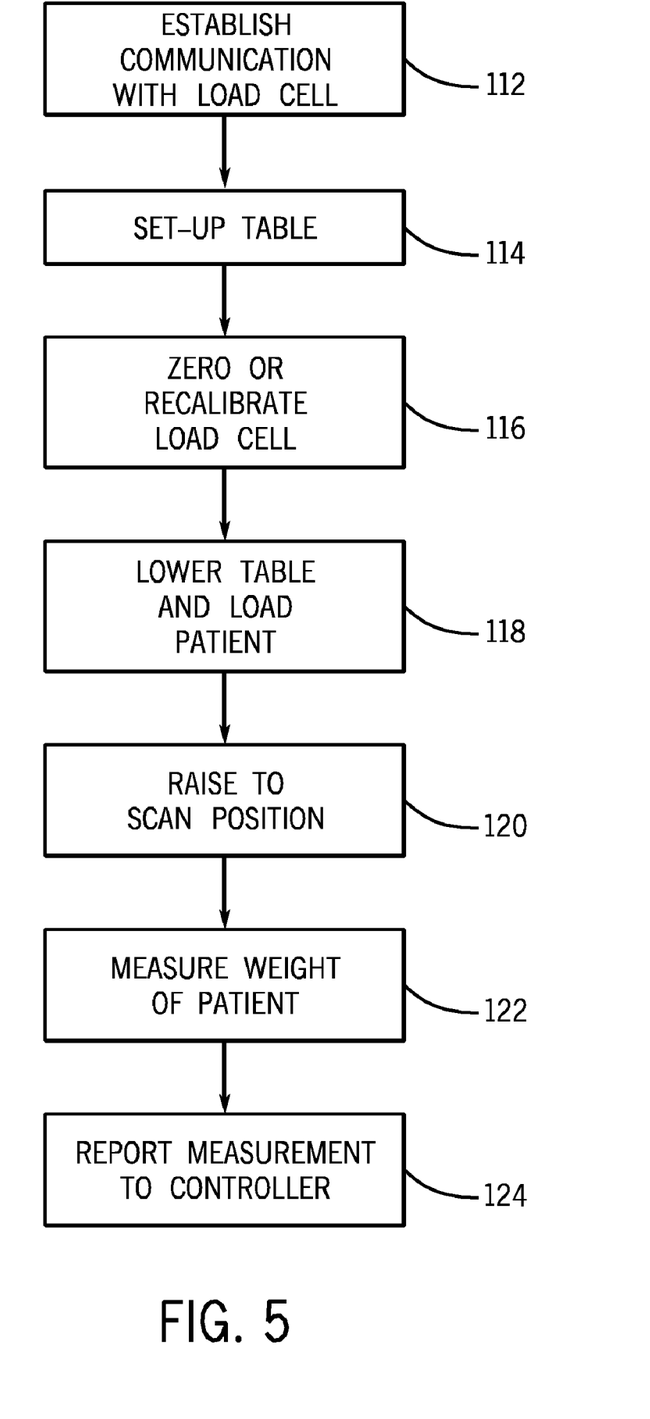
FIG. 5 is a flow chart illustrating a method of using one or more of the embodiments illustrated in FIGS. 1-4.

FIG. 5 is a flow chart illustrating a method of using one or more of the embodiments of the integrated weight system illustrated in FIG. 1. The operator establishes communications with load cell 18 (block 112) and sets-up the table assembly 16 to receive patient 70 (block 114). In this manner, the operator may establish a connection via load cell interface circuit 72 to modality system controller 14. Next, the operator may zero or recalibrate load cell 18 (block 116). As discussed above, zeroing and/or recalibrating load cell 18 may be desirable to facilitate use of the load cell and compensate for the weight of the table or tables, any components on the tables, drift, or any other factors that would otherwise appear to increase or reduce the patient weight measurement. However, zeroing or recalibrating is not an absolute requirement and can be handled by other techniques.

The operator then lowers upper table 44 and loads patient 70 in preparation for the imaging procedure (block 118). The operator then raises the upper table 44 to the scan position via lifting cylinder 38, or any other appropriate lifting mechanism, as described above (block 120). Once in the scan position, the operator then measures the weight of patient 70 (block 122) to be used for imaging correction and/or to determine the allowed cantilever position of scanning table 46. Finally, the load cell interface circuit 72 may communicate the weight of patient 70 to modality system controller 14 and/or the operator may input the weight via workstation 22. In sum, modality system controller 14 is provided feedback via load cell interface circuit 72 to determine the weight of the patient. The controller may thus make adjustments to the system settings automatically, or in a semi-automated fashion (e.g., with operator intervention).

An additional benefit of embodiments of the present invention is that calibrations and corrections may be modified (e.g., scatter, dual energy decomposition parameters, etc.) based the weight of the patient. Specifically, the weight of the patient may be used to select parameters for post-processing algorithms such as computer assisted diagnosis (CAD), noise reduction, and contrast enhancement.

Figure 6:
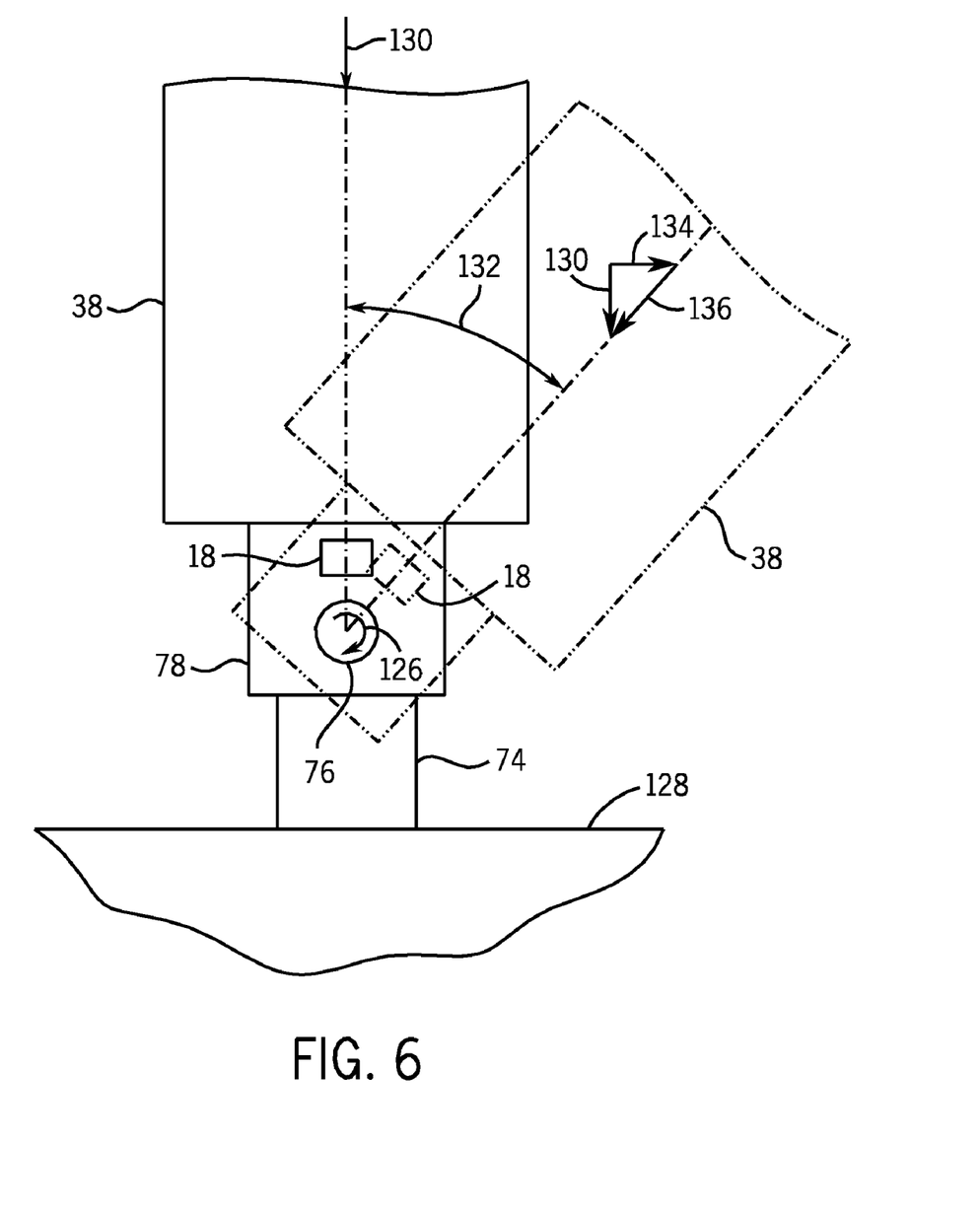
FIG. 6 is an elevational view of the lifting mechanism of FIG. 1, illustrating the lifting mechanism in two different positions and the resulting force components placed on the lifting mechanism due to the weight of a patient.

FIG. 6 illustrates possible multi-component or off-axis loading that may be corrected by using embodiments of the present invention. The figure illustrates load cell 18 positioned on clevis 78 which rotates about pin 76, as generally represented by reference numeral 126. When lifting cylinder 38 is perpendicular to the ground 128, the weight of patient 70, generally represented by reference numeral 130, is transmitted along the axis of the lifting cylinder. In other words, there is not a horizontal component and the weight is a single force component that is measured by load cell 18. FIG. 6 further illustrates lifting cylinder 38 in a second position after being rotated about the axis of pin 76. As illustrated, the second position of cylinder 38 is at a different angle than the first position with respect to ground 128, as generally represented by reference numeral 132. When lifting mechanism 38 is in this position, the weight of patient 130 now includes both a horizontal component and a vertical component, generally represented by reference numerals 134 and 136, respectively. In other words, the weight measured by load cell 18 may not accurately reflect the weight of patient 70 if the multi-component force is not correctly determined.

There are a number of ways to correct for multi-component loading, or more properly, loading at different angles of the support or raising structure. One is to use multiple load cells to detect loading in each axis and then to calculate the normal force using vector mechanics. Another method is to determine the relative position of the lifting mechanism 38 and the resulting angle 132 from perpendicular and to compute the weight based on the simple trigonometric relationship of the component forces. For example, table assembly 16 may incorporate sensors to determine the angular position of weight lifting cylinder 38 with respect to ground 128. The correction can then be used to calculate the actual weight of patient 70 based on the angular position 132 of lifting cylinder 38. Thus, embodiments of the present invention enable an operator to correct for the angular position of lifting cylinder 38 or provide weight sensing element 18 that automatically corrects with this. Furthermore, depending on the configuration of lifting cylinder 38, a correction may not be required because the weight of the patient may be oriented so that there is never a horizontal component, or so that the angle of incline of the support or raising structures on which the load sensing means is placed remains constant.

Another method is to orient the legs of the Wheatstone bridge so that each resistive element measures the strain in a particular axis and the weight calculation is internally corrected by the Wheatstone bridge. As illustrated in FIG. 4, the Wheatstone bridge may include multiple active resistive components 88, 90, 92, and 94. Each active resistive component may be oriented on clevis 78 to measure strain in a specific direction. In such a scenario, the result is that the Wheatstone bridge automatically corrects for multi-component loading based on the summation of the measured resistance. In other words, the resistance in one leg might increase, due to an increase in strain in that axis, while the resistance in another leg might decrease, due to a decrease in strain in that axis with the Wheatstone bridge providing the net change in resistance and/or automatically correcting for the multi-component loading. Similarly, multiple load cells may be implemented and the measured weight from each load cell could be used to determine the weight of the patient. In sum, embodiments of the present invention may include any of these methods, or others, and are not limited to the ones disclosed.

While only certain features of the invention have been illustrated and described herein, many modifications and changes will occur to those skilled in the art. It is, therefore, to be understood that the appended claims are intended to cover all such modifications and changes as fall within the true spirit of the invention. By way of example, the invention is not intended to be limited to any particular type of design of lifting mechanism or table structure. Similarly, various sensors may be associated with the patient support structures to provide reliable weight-indicative signals.

The invention claimed is:

1. A medical imaging system, comprising:
a table assembly including a lifting mechanism for positioning a patient within a medical imaging modality, and a scanning table configured to move parallel to, and to cantilever from, a support coupled to the scanning table;
a load cell mechanically coupled to the table assembly, the load cell configured to measure and indicate the weight of the patient;
a processor in communication with the load cell and configured to adjust an imaging parameter based on the weight of the patient; and
a control system in communication with the table assembly and configured to inhibit extension of the scanning table from the support beyond a threshold distance, wherein the control system is configured to receive the weight of the patient from the load cell and to automatically calculate the threshold distance based on the weight of the patient.

2. The system of claim 1, wherein the table assembly comprises a base and an upper table, the base being coupled to the upper table via linkages and the lifting mechanism, the scanning table being supported by the upper table and configured to move parallel to the upper table and cantilever therefrom.

3. The system of claim 2, wherein the base includes a fixed clevis that is coupled to a rotating clevis of the lifting mechanism, the load cell being mechanically coupled to the fixed clevis or any portion of the base.

4. The system of claim 2, wherein the base includes a fixed clevis that is coupled to a rotating clevis of the lifting mechanism, the load cell being mechanically coupled to the rotating clevis or any portion of the lifting mechanism.

5. The system of claim 1, wherein the table assembly includes a device in communication with the load cell and/or processor and configured to display the weight of the patient.

6. The system of claim 1, wherein the table assembly and/or the processor include an operator interface for zeroing or recalibrating the load cell.

7. The system of claim 1, wherein the lifting mechanism includes a screw drive.

8. The system of claim 1, wherein the lifting mechanism includes a hydraulic cylinder.

9. The system of claim 1, wherein the load cell includes at least one Wheatstone bridge.

10. The system of claim 9, wherein the Wheatstone bridge is oriented to detect multi-component loading.

11. The system of claim 1, wherein the load cell includes at least one strain gage.

12. The system of claim 1, wherein the medical imaging modality comprises a computed tomography scanner, an X-ray scanner, a positron emission tomography scanner, or a magnetic resonance imaging scanner.

13. A medical imaging system, comprising:
a table assembly including a lifting mechanism used to position a patient within a medical imaging modality, and a scanning table configured to move parallel to, and to cantilever from, a support coupled to the scanning table;
a load cell mechanically coupled to the table assembly;

an interface circuit coupled to the load cell and configured to derive a signal representative of patient weight from output signals from the load cell;

a processor in communication with the interface circuit and configured to adjust an imaging parameter based on the weight of the patient; and a control system in communication with the table assembly and configured to inhibit extension of the scanning table from the support beyond a threshold distance calculated by the control system based on the weight of the patient, wherein the control system includes an actuator coupled to the table assembly and configured to extend and to retract the scanning table with respect to the support in response to an input signal, and wherein the control system includes a controller programmed to automatically limit extension of the scanning table by the actuator beyond the calculated threshold distance.

14. The system of claim 13, wherein the table assembly comprises a base and an upper table, the base being coupled to the upper table via linkages and the lifting mechanism, the scanning table being supported by the upper table and configured to move parallel to the upper table and cantilever therefrom.

15. The system of claim 14, wherein the base includes a fixed clevis that is coupled to a rotating clevis of the lifting mechanism, the load cell being mechanically coupled to the fixed clevis or any portion of the base.

16. The system of claim 14, wherein the base includes a fixed clevis that is coupled to a rotating clevis of the lifting mechanism, the load cell being mechanically coupled to the rotating clevis or any portion of the lifting mechanism.

17. The system of claim 13, wherein the load cell comprises at least one strain gage.

18. A method for controlling a medical imaging system comprising:

positioning a table assembly via a lifting mechanism to a first position to load a patient;

positioning the table assembly via the lifting mechanism to a second position;

transmitting a signal from a load cell disposed on the table assembly to control circuitry for controlling acquisition of image data;

setting imaging parameters based on the weight of the patient; and adjusting imaging parameters based on the weight of the patient using post-processing algorithms that include computer aided diagnosis, noise reduction, or contrast enhancement.

19. The method of claim 18, comprising zeroing and/or recalibrating the load cell.

20. The method of claim 18, wherein the load cell includes at least one strain gage.

21. The method of claim 18, comprising resolving an output signal from the load cell to compute patient weight.

22. The method of claim 18, wherein the lifting mechanism is a screw thread or a hydraulic cylinder.

23. The method of claim 18, wherein the imaging parameter is set automatically without operator intervention.

24. A medical imaging system, comprising:

a table assembly including a lifting mechanism for positioning a patient within a medical imaging modality, and a scanning table configured to move parallel to, and to cantilever from, a support coupled to the scanning table;

a load cell mechanically coupled to the table assembly, the load cell configured to measure and indicate the weight of the patient; and a control system in communication with the table assembly and configured to inhibit horizontal extension of the scanning table from the support beyond a threshold distance calculated by the control system based on the weight of the patient.

25. The medical imaging system of claim 24, wherein the control system includes an electromechanical interlock coupled to the table assembly and configured to receive an input signal based on the threshold distance.

26. The medical imaging system of claim 24, wherein the control system includes an actuator coupled to the table assembly and configured to extend and to retract the scanning table with respect to the support in response to an input signal, and wherein the control system includes a controller programmed to automatically limit extension of the scanning table by the actuator beyond the calculated threshold distance.

27. The medical imaging system of claim 24, wherein the control system is configured to receive the weight of the patient from the load cell and to automatically calculate the threshold distance based on the weight of the patient.

* * * * *